United States Patent
Arboleda et al.

(10) Patent No.: US 10,433,799 B2
(45) Date of Patent: Oct. 8, 2019

(54) TILTED-GRATING APPROACH FOR SCANNING-MODE X-RAY GRATING INTERFEROMETRY

(71) Applicant: PAUL SCHERRER INSTITUT, Villigen Psi (CH)

(72) Inventors: Carolina Arboleda, Zurich (CH); Marco Stampanoni, Endingen (CH); Zhentian Wang, Brugg (CH)

(73) Assignee: Paul Scherrer Institut, Villigen PSI (CH)

( * ) Notice: Subject to any disclaimer, the term of this patent is extended or adjusted under 35 U.S.C. 154(b) by 393 days.

(21) Appl. No.: 15/309,222

(22) PCT Filed: Feb. 25, 2015

(86) PCT No.: PCT/EP2015/053909
§ 371 (c)(1),
(2) Date: Nov. 7, 2016

(87) PCT Pub. No.: WO2015/169463
PCT Pub. Date: Nov. 12, 2015

(65) Prior Publication Data
US 2017/0082559 A1    Mar. 23, 2017

(30) Foreign Application Priority Data
May 7, 2014  (EP) .................................... 14167372

(51) Int. Cl.
*A61B 6/00* (2006.01)
*G01N 23/04* (2018.01)
*G21K 1/02* (2006.01)

(52) U.S. Cl.
CPC .......... *A61B 6/4291* (2013.01); *A61B 6/4035* (2013.01); *A61B 6/484* (2013.01);
(Continued)

(58) Field of Classification Search
CPC ... A61B 6/4035; A61B 6/4208; A61B 6/4291; A61B 6/484; G01N 2223/303;
(Continued)

(56) References Cited

U.S. PATENT DOCUMENTS

2009/0092227 A1* 4/2009 David .................. A61B 6/4233
378/36
2011/0235780 A1   9/2011 Tada
(Continued)

*Primary Examiner* — Chih-Cheng Kao
(74) *Attorney, Agent, or Firm* — Lawrence Greenberg Werner Stemer; Ralph Locher

(57) ABSTRACT

Among the existent X-ray phase-contrast modalities, grating interferometry appears as a promising technique for commercial applications, since it is compatible with conventional X-ray tubes. However, since applications such as medical imaging and homeland security demand covering a considerable field of view, the fabrication of challenging and expensive large-area gratings would be needed. A scanning setup is a good solution, because it uses cheaper line detectors instead of large-area 2D detectors and would require smaller gratings. In this setup, the phase-retrieval using the conventional phase-stepping approach would be slow, so having a faster method to record the signals becomes fundamental. To tackle this problem, a scanning-mode grating interferometer configuration is used, in which a grating is tilted to form Moire fringes perpendicular to the grating lines. The sample is then translated along the fringes, so each line detector records a different phase step for each slice of the sample.

8 Claims, 2 Drawing Sheets

(52) U.S. Cl.
CPC ............ G01N 23/04 (2013.01); G21K 1/025 (2013.01); *A61B 6/4208* (2013.01); *G21K 2207/005* (2013.01)

(58) Field of Classification Search
CPC ...... G01N 23/04; G01N 23/083; G21K 1/025; G21K 1/067; G21K 2207/005
See application file for complete search history.

(56) References Cited

U.S. PATENT DOCUMENTS

2011/0243305 A1* 10/2011 Tada .................... A61B 6/4291
378/87
2013/0028378 A1 1/2013 Stutman et al.

* cited by examiner

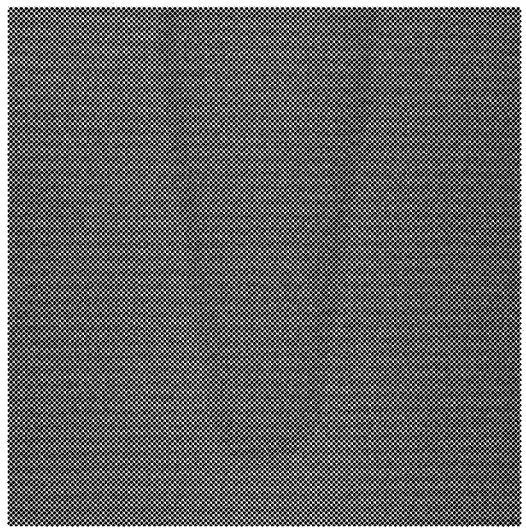
FIG. 3
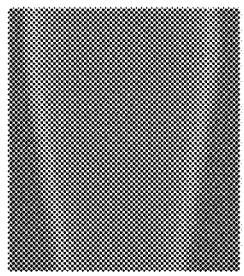 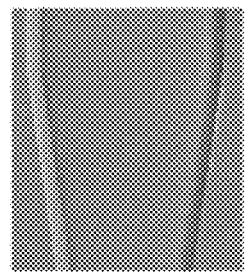 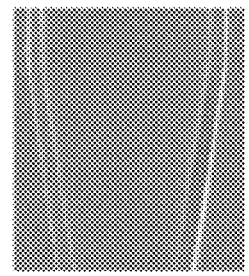
FIG. 4A      FIG. 4B      FIG. 4C

TILTED-GRATING APPROACH FOR SCANNING-MODE X-RAY GRATING INTERFEROMETRY

BACKGROUND OF THE INVENTION

Field of the Invention

The present invention relates to a method and a system to retrieve absorption, DPC and dark field signals obtained by a grating interferometer.

Grating interferometry constitutes a very promising technique for commercial X-ray phase-contrast applications, since it works with traditional X-ray tubes, is mechanically robust and has modest requirements for mono-chromaticity and spatial coherence. In the last few years, several exciting applications of this technique have been reported, ranging from material inspection to medical imaging.

To carry out the transition of grating interferometry from the laboratory to the commercial setting, it has to be tailored to cover a large field of view (FOV) and allow reasonable exposure times. To fulfill these requirements, a scanning setup would be an excellent choice, since it requires line instead of 2D detectors and would avoid the fabrication of large-area gratings, which might be laborious and pricey. On the other hand, in order to retrieve different contrast signals, conventional grating interferometry requires a phase-stepping procedure, in which one of the gratings is translated stepwise (in sub-micron scale) and an image is acquired for each step. This procedure is time-consuming in general and demands high system stability and accuracy, so it constitutes a major problem for the implementation of grating interferometry in a commercial setting. A scanning-mode method able to "hard-code" the phase-stepping procedure into a one-dimension scan [1,] can fundamentally solve the problem.

In this regard, Kottler et al [2] introduced a scanning-mode grating interferometry setup. They propose a method in which a Moiré fringe parallel to the grating lines is generated by slightly changing the theoretical inter-grating distance. In this arrangement, equidistantly distributed lines of the detector correspond to different relative positions of the phase and absorption gratings, which can be regarded as phase-steps. Therefore, by translating the sample in a direction perpendicular to the fringe orientation, a phase-stepping curve can be retrieved and Fourier-Component Analysis (FCA) can be used to reconstruct the signals.

Another possibility to solve this issue is to use a staggered grating, so that the grating is located at a different lateral position for each line detector, and a phase stepping curve can be retrieved by scanning the sample in a direction perpendicular to the grating lines. However, this approach implies the fabrication of gratings with a novel design which will be hard to align, and kept as such, with the line detectors.

As mentioned above, to transfer the X-ray grating interferometry technology to a commercial setting, it is necessary to make it suitable to image large field-of-views. To achieve this goal while using the current grating interferometry implementation, large-area gratings would be needed, but they are difficult and pricey to fabricate. Therefore, it would be ideal to avoid the fabrication of this kind of gratings.

Managing to integrate the grating interferometer technology into a scanning setup certainly avoids this issue. However, its integration involves the development of a new signal retrieval method, because the conventional retrieval method would be inefficient in this setup.

BRIEF SUMMARY OF THE INVENTION

It is therefore the objective of the present invention to provide a system and a method for retrieving absorption, DPC and dark field signals obtained by a grating interferometer.

This objective is achieved according to the present invention by a method and a system that use a tilted-grating-based scanning method for grating interferometry as given in the main method claim and the main system claim. The general idea is to generate a Moire fringe perpendicular to the grating lines by tilting one of the gratings, so that each line detector of the detector ends up recording a different phase step as the sample is translated during the scan.

Preferred embodiments of the present invention are listed in the dependent claims.

BRIEF DESCRIPTION OF THE SEVERAL VIEWS OF THE DRAWING

Preferred examples of the present invention are hereinafter described with reference to the attached drawings which depict in:

FIG. 3 schematically a Moiré pattern generated with the tilted-grating method; and FIG. 4 schematically the absorption, DPC and dark-field images acquired with the tilted-grating method.

DESCRIPTION OF THE INVENTION

Figure 1:
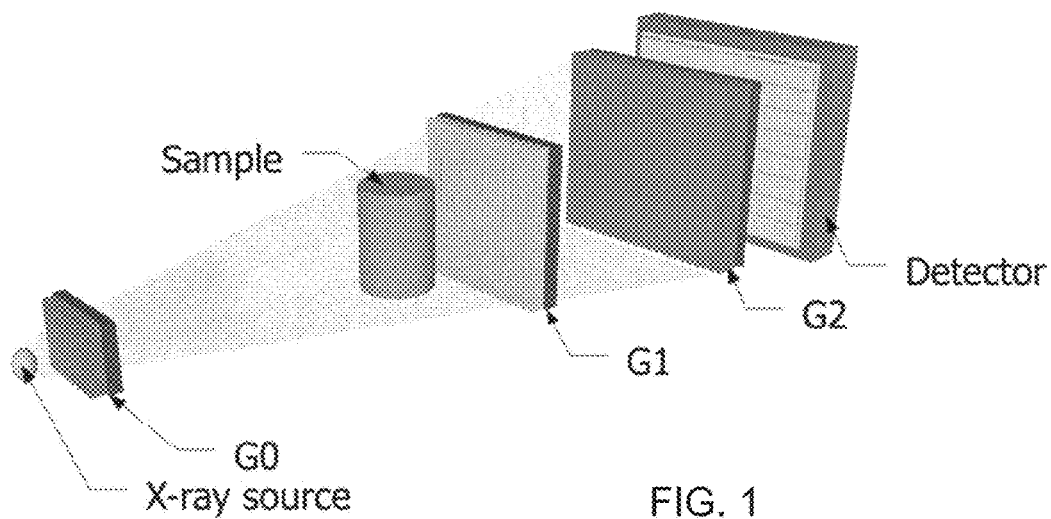
FIG. 1 schematically a sketch of an X-ray grating interferometer having a tilted grating.

A standard grating interferometer is shown in FIG. 1, comprising a source grating G0, a phase grating G1 and an absorption grating G2. The use of source grating G0 is optional, depending on the spatial coherence properties of the X-ray source. During the scanning of a sample, the illumination generated by the X-ray source is recorded by a detector disposed downstream of the absorption grating G2. The scanning approach is achieved by moving one of the gratings stepwise with respect to the recorded images along one period of the analyzer grating G1 in a direction perpendicular to the line of the phase grating G1.

Figure 2:
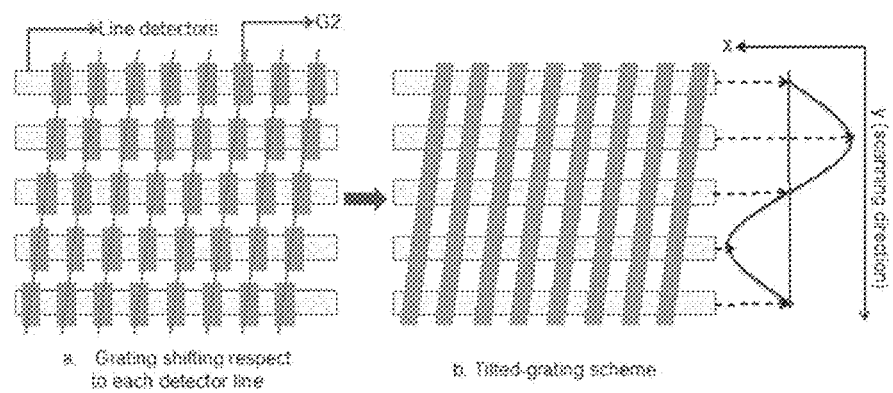
FIG. 2 schematically the essential feature of the tilted grating in a tilted-grating method.

The general idea behind the tilted-grating design is illustrated in FIG. 2. FIG. 2(a) schematically shows a sketch of a staggered grating G2, where the grating at a different lateral position covers each detector line. In FIG. 2(b) the same effect is achieved, when the analyzer grating G2 is tilted according to the present invention so that each line detector records a different phase step (red dots on the phase-stepping curve shown on the right).

If a staggered grating is used (see FIG. 2a) [3], such that each line detector is covered by the grating at a different position in x direction, the phase-stepping approach is mimicked by scanning the sample along y direction, without the need of moving the analyzer grating G2, and will end up having each line detector record a different phase step for each slice of the sample, as long as the grating lines are subsequently shifted by a distance $\delta_x$, defined as:

$$\delta_x = m\frac{p_2}{n}$$

where n is the number of line detectors, so that the whole staggered grating is covering an integer number m of periods $p_2$ of the analyzer grating G2. Since the fabrication of this staggered grating and its successive alignment to the corresponding line detectors might become very challenging, an easier way according to the present invention to achieve the same effect is to tilt of the analyzer grating G2, as shown in FIG. 2b. Assuming the present line detectors are separated by a distance D, the tilting angle θ can be calculated as:

$$\theta = \arctan\left(\frac{\delta_x}{D}\right)$$

To compensate for the beam divergence, the sample-translation step s must be adjusted to:

$$s = D\frac{L}{L+d}$$

where L is the source-to-G1 distance and d represents the inter-grating distance. Afterwards, the absorption, DPC and dark-field signals can be retrieved by standard FCA. A reference image (i.e. no sample in the beam) has to be acquired as well in order to subtract the background phase distribution, like in the phase-stepping approach.

Recapitulating, the procedure is started by acquiring a reference image and retrieving the background phase-stepping curve. Afterwards, a tilting angle is calculated based on the hardware (i.e. the number of line detectors disposed in the detector and the separation between the line detectors) and the number of periods $p_2$ to be covered. Subsequently, the analyzer grating G2 is tilted and the sample is moved along y direction (see FIG. 2 right side) by successive steps s until the signal corresponding to each slice has been recorded by the number of line detectors used for the calculations, so that a sample phase-stepping curve for each slice can be retrieved. Rearranging the acquired data, the absorption, DPC and dark-field signals can be reconstructed by performing FCA in two dimensions.

An example of the Moiré fringe generated with this tilted grating method is shown in FIG. 3 and the corresponding reconstructed absorption, DPC and dark-field images acquired with the tilted-grating method are displayed in FIG. 4.

Grating-based X-ray imaging setups like the one shown in FIG. 1 can generate three different signals: the conventional absorption contrast (AC) signal, the differential phase contrast (DPC) signal caused by refraction due to phase shifts, and the small-angle scattering contrast (SC) signal (also named dark-field signal) caused by scattering from inhomogeneities in the sample.

Interferometer grating setups with two gratings (G1 and G2) or three gratings (G0, G1, and G2) can be used to record the deflection of the X-rays. In the case of a two-grating setup, the source needs to fulfill certain requirements regarding its spatial coherence. The source grating G0 is required, when the source size is bigger than $p_2 * L/d$, where $p_2$ is the period of G2, L is the distance between the source and G1, and d is the distance between G1 and G2. In a three-grating setup no spatial coherence is required. Therefore, the three-grating setup is suited for use with incoherent X-ray sources, in particular with standard X-ray tubes.

To separate the conventional attenuation contrast (AC) from the DPC and SC contrast, a phase-stepping approach is carried out. One of the gratings is displaced transversely to the incident beam whilst acquiring multiple images. The intensity signal at each pixel in the detector plane oscillates as a function of the displacement. The average value of the oscillation represents the AC. The phase of the oscillation can be directly linked to the wave-front phase profile and thus to the DPC signal. The amplitude of the oscillation depends on the scattering of X-rays in the object and thus yields the SC signal.

For the (two or three) gratings, several variations have been proposed and applied. The source grating G0 (if required) is the one closest to the X-ray source. It usually consists of a transmission grating of absorbing lines with the period $p_0$. It can be replaced by a source that emits radiation only from lines with the same period. The phase grating G1 is placed further downstream of the X-ray source. It consists of lines with a period $p_1$. The analyzer grating G2 is the one most downstream of the setup. It usually consists of a transmission grating of absorbing lines with the period $p_2$. It can be replaced by a detector system that has a grating-like sensitivity with the same period.

Two regimes of setups can be distinguished: In the so called "near-field regime" and the "Talbot regime". In the "near-field regime", the grating period p, grating distances d and the x-ray wavelength λ are chosen such that diffraction effects are negligible. In this case, all gratings need to consist of absorbing lines. In the "Talbot regime", diffraction from the grating structures is significant.

Here, the phase grating G1 should consist of grating lines that are either absorbing or, preferentially, phase shifting. Several amounts of phase shift are possible, preferentially π/2 or multiples thereof. The grating periods must be matched to the relative distances between the gratings. In the case of setups in the "Talbot regime", the Talbot effect needs to be taken into account to obtain good contrast. The formulae for the grating periods and distances are described in [4].

It has to be noted that a sharp distinction between the two regimes is not easily given, as the exact criterion depends on the duty cycle of the grating structure, and whether the gratings are absorbing or phase shifting. E.g., for a grating with absorbing lines and a duty cycle of 0.5, the condition for the "near field regime" is $d \geq p^2/2\lambda$.

The sample is mostly placed between the source grating G0 and the phase grating G1 (or upstream of the phase grating G1 in the case of a two-grating set-up), however it can be advantageous to place it between the phase grating G1 and the analyzer grating G2 [5].

The presented invention is relevant in all of the aforementioned cases, i.e. in the two- and three-gratings case, in the case of the "near-field regime" and the "Talbot regime", and for the sample placed upstream or downstream of G1.

Intensity curves (with and without sample) are usually obtained with "phase stepping" methods or alternative techniques. Defining for each pixel on the detector the mean, phase and visibility of the intensity curve with sample as $I_s, \Phi_s, V_s$, and without sample as $I_b, \Phi_b, V_b$, yields:

$$AC = -\log\left(\frac{I_s}{I_b}\right)$$

$$DPC = \Phi_s - \Phi_b$$

$$SC = -\log\left(\frac{V_s}{V_b}\right).$$

For both the AC signal and SC signal, the valid data range is [0,+∞], while for the DPC it is [−π,+π]. Images obtained by plotting such signals are all perfectly registered.

A similar way to generate these multiple information signals can be found in diffraction enhanced imaging where the equivalent of the intensity curve is named the rocking curve.

REFERENCES

[1] E. Roessl, H. Daerr, T. Koehler, G. Martens and U. van Stevendaal, "Slit-scanning differential phase-contrast mammography: First experimental results," Proc. SPIE 9033, 90330C (2014).
[2] C. Kottler, F. Pfeiffer, O. Bunk, C. Grünzweig, C. David, "Grating interferometer based scanning setup for hard X-ray phase contrast imaging," Rev. Sci. Instrum. 78, 043710 (2007).
[3] C. David and F. Pfeiffer, "X-ray interferometer for phase contrast imaging," Patent WO 2008/006470 A1 (17, Jan. 2008).
[4] T. Weitkamp, C. David, C. Kottler et al., "Tomography with grating interferometers at low-brilliance sources", 6318, 6318S (2006).
[5] C. David, Optimierte Anordnung von Gittern für die Phasenkontrastbildgebung im Röntgenbereich, Europäische Patentanmeldung EP 2 168 488 A1.

The invention claimed is:

1. A grating interferometer system for obtaining absorption, differential phase contrast (DPC) and dark-field data from quantitative X-ray images from a sample, the grating interferometer system comprising:
an X-ray source;
gratings including one of:
a phase grating and an analyzer grating; or
a source grating, said phase grating and said analyzer grating;
a position-sensitive detector;
means for recording images of said position-sensitive detector;
means for evaluating intensities for each pixel in a series of the quantitative X-ray images, in order to identify characteristics of an object for each individual pixel as at least one of an absorption-dominated pixel, a DPC-dominated pixel, and an X-ray dark-field dominated pixel;
means to tilt either said phase grating or said analyzer grating by a predetermined angle; and
means to move the sample, said x-ray source, or said gratings and said position-sensitive detector to perform a scanning of a probe; and
wherein for near-field-regime operation, a distance between said gratings is chosen freely within the near-field-regime, and a Talbot-regime is chosen according to:

$$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda}$$

where $n = 1, 3, 5 \ldots$, and $$\eta = \begin{cases} 1 & \text{if the phase shift of } G_1 \text{ is } (2l-1)\frac{\pi}{2}, p_2 = \frac{L + D_{n,sph}}{L} p_1 \\ 2 & \text{if the phase shift of } G_1 \text{ is } (2l-1)\frac{\pi}{2}, p_2 = \frac{L + D_{n,sph}}{L} \end{cases}$$

where l=1, 2, 3 ..., $D_n$ is an odd fractional Talbot distance when a parallel X-ray beam is used, G1 is said phase grating, $D_{n,sph}$ is when a fan or cone X-ray beam is used and L is a distance between said source grating and said phase grating.

2. The system according to claim 1, wherein said phase grating is a line grating, an absorption grating or a phase grating that is a low-absorption grating but generating a considerable X-ray phase shift and of Π or odd multiples thereof.

3. The system according to claim 1, wherein said analyzer grating is a line grating having a high X-ray absorption contrast with its period being a same as that of a self-image of said phase grating, wherein said analyzer grating is placed closely in front of said position-sensitive detector with its lines parallel to those of said phase grating, before tilting said phase grating or said analyzer grating.

4. The system according to claim 1, wherein said position-sensitive detector is a line sensitive detector.

5. A method to retrieve absorption, differential phase contrast (DPC) and dark field signals from a Moire fringe pattern obtained by detuning a grating interferometer system having an X-ray source, a phase grating, an analyzer grating and a line sensitive detector, which comprises the steps of:
producing the Moire fringe pattern of a desired period by tilting one of the phase grating or the analyzer grating by a predetermined angle; and
calculating a tilting angle using:
a period $P_2$ of the analyzer grating;
a number n of detector lines;
a number m of the periods $P_2$ that are to be covered;
a separation D between the detector lines of the line sensitive detector;
and employing formulas:

$$\delta_x = m \frac{p_2}{n}$$

$$\theta = \arctan\left(\frac{\delta_x}{D}\right)$$

where θ is the tilting angle; and
scanning either a sample or the grating interferometer system along the Moire fringe pattern.

6. The method according to claim 5, which further comprises using reference and sample data acquired with the grating interferometer system to retrieve the absorption, the DPC and the dark-field signals by Fourier Component analysis.

7. The method according to claim 5, wherein:
the grating interferometer system has the phase grating and the analyzer grating, and one of the phase grating and the analyzer grating is tilted; or
the grating interferometer system has a source grating, the phase grating and the analyzer grating, and wherein:
only the phase grating is tilted; or
only the analyzer grating is tilted; or
a pair of the source grating and the phase grating is tilted; or a pair of the phase grating and the analyzer grating is tilted.

8. The method according to claim 5, wherein compatible with radiography, tomosynthesis and computed tomography, either the sample or the grating interferometer system is rotated to acquire multiples views.

* * * * *